(12) United States Patent
Ihara

(10) Patent No.: US 9,355,458 B2
(45) Date of Patent: May 31, 2016

(54) IMAGE PROCESSING APPARATUS, METHOD AND PROGRAM

(71) Applicant: FUJIFILM Corporation, Tokyo (JP)

(72) Inventor: Satoshi Ihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/657,619

(22) Filed: Mar. 13, 2015

(65) Prior Publication Data

US 2015/0187085 A1 Jul. 2, 2015

Related U.S. Application Data

(63) Continuation of application No. PCT/JP2013/005294, filed on Sep. 6, 2013.

(30) Foreign Application Priority Data

Sep. 20, 2012 (JP) .................. 2012-207155

(51) Int. Cl.
*G06K 9/00* (2006.01)
*G06T 7/00* (2006.01)
*A61B 5/055* (2006.01)
(Continued)

(52) U.S. Cl.
CPC ............... *G06T 7/0093* (2013.01); *A61B 5/055* (2013.01); *A61B 5/08* (2013.01); *G06T 7/004* (2013.01); *G06T 7/0083* (2013.01); *G06T 7/0085* (2013.01); *G06T 17/05* (2013.01); *G06T 19/00* (2013.01); *A61B 2576/02* (2013.01); *G06T 2207/10072* (2013.01);
(Continued)

(58) Field of Classification Search
None
See application file for complete search history.

(56) References Cited

U.S. PATENT DOCUMENTS

| 6,711,300 B2 * | 3/2004 | Fisher .............. H04N 21/23412 348/405.1 |
| 2003/0048849 A1 * | 3/2003 | Tomita, Jr. ............ G06T 7/2033 375/240.25 |

(Continued)

FOREIGN PATENT DOCUMENTS

| JP | 2010-220742 A | 10/2010 |
| JP | 2011-098195 A | 5/2011 |
| WO | 2012/115592 A1 | 8/2012 |

OTHER PUBLICATIONS

Daisuke Kobayashi, et al., "Tree-Graph Representation of Main-Sub Trunk Type 3D Blood Vessels by Route-Based Approach", The Transactions of the Institute of Electronics, Information and Communication Engineers, 2009, pp. 511-520, vol. J92-D, No. 4.

(Continued)

*Primary Examiner* — Hadi Akhavannik
(74) *Attorney, Agent, or Firm* — Sughrue Mion, PLLC

(57) ABSTRACT

A path detection-use graph structure is generated based on a plurality of nodes representing the plurality of linear structures, and a path that is included in the generated path detection-use graph structure and connects a plurality of root nodes representing points of origin of the plurality of linear structures to each other is detected. Then, based on a predetermined condition representing a feature of an erroneous connection edge erroneously connecting two nodes that are to belong to different graph structures to each other, a connection cost is set for each of edges forming the path so that the erroneous connection edge is hard to connect, and based on the set connection costs, the plurality of graph structures corresponding respectively to the plurality of linear structures are generated.

11 Claims, 5 Drawing Sheets

(51) Int. Cl.
*A61B 5/08* (2006.01)
*G06T 17/05* (2011.01)
*G06T 19/00* (2011.01)

(52) U.S. Cl.
CPC .......... *G06T 2207/20072* (2013.01); *G06T 2207/30101* (2013.01); *G06T 2210/41* (2013.01)

(56) References Cited

U.S. PATENT DOCUMENTS

| | | | | |
|---|---|---|---|---|
| 2005/0074162 | A1* | 4/2005 | Tu | G06T 7/0018 382/154 |
| 2010/0296709 | A1* | 11/2010 | Ostrovsky-Berman | G06T 7/0081 382/128 |
| 2011/0085701 | A1 | 4/2011 | Kitamura | |
| 2011/0135172 | A1 | 6/2011 | Kitamura | |
| 2013/0064428 | A1 | 3/2013 | Kitamura | |

OTHER PUBLICATIONS

Tsutomu Inoue, et al., "Robust Bronchus Extraction using Machine Learning and Minimum Spanning Tree", IEICE Technical Report, Jan. 12, 2012, pp. 215-220, vol. 111, No. 389.

Andrzej Szymczak, et al., "Coronary vessel trees from 3D imagery: A topological approach", Medical Image Analysis, Aug. 2006, pp. 548-559, vol. 10, No. 4.

International Search Report, PCT/JP2013/005294 dated Nov. 19, 2013 [PCT/ISA/210].

\* cited by examiner

IMAGE PROCESSING APPARATUS, METHOD AND PROGRAM

CROSS REFERENCE TO RELATED APPLICATIONS

The present application is a Continuation of PCT International Application No. PCT/JP2013/005294 filed on Sep. 6, 2013, which claims priority under 35 U.S.C. §119(a) to Japanese Patent Application No. 2012-207155 filed on Sep. 20, 2012. Each of the above application(s) is hereby expressly incorporated by reference in its entirety, into the present application.

TECHNICAL FIELD

The present invention relates to an image processing apparatus, method, and a program for constructing a specific structure detected from image data as a graph structure. In particular, the present invention relates to an image processing apparatus, method, and program for constructing a graph structure for each of a plurality of specific structures that are located close to each other. The plurality of specific structures are, for example, a portal vein and hepatic veins of liver, or other such structures, whose blood vessel branches run close to each other in such a manner as to be entangled with each other.

BACKGROUND ART

When a surgery is performed on an organ, such as liver or lung, to resect an affected region, the following operation is required in the case of the liver, for example. Specifically, blood vessels, hepatic parenchyma, and a tumor region are extracted from an X-ray CT image of the liver, and based on the positions of core lines, diameters, and the like of the extracted blood vessels, a blood vessel that dominates the extracted tumor region is identified. In this manner, the blood vessel that supplies nutrition to the tumor is identified, and the region dominated by the identified blood vessel is determined appropriately as a region to be resected. In the surgery of resecting a region of the liver, this operation is necessary in order to appropriately resect a portion of a portal vein that supplies nutrition to the tumor and a region that is dominated by the portion of the portal vein and may be supplied with substances to be noted such as cancer cells, in such a manner as to maintain the function of the liver even after the resection. For this reason, it is important to perform a thorough simulation as to which region of the organ is to be resected before the surgery. Further, in order to perform this simulation, it is necessary to extract central paths of the blood vessels running in the lung and the liver accurately.

As an image recognition technology for extracting a linear structure such as bronchi from a three-dimensional medical image acquired by CT or the like, there has been proposed a method using a Hessian matrix as disclosed in Patent Literatures 1 and 2.

According to the method disclosed in Japanese Patent Application Publication No. 2010-220742, first, after a three-dimensional medical image is subjected to multi-resolution transformation, eigenvalues of a Hessian matrix are analyzed in an image of each resolution to extract linear structure elements. Each of those linear structure elements has such a feature that only one of three eigenvalues obtained by the eigenvalue analysis is close to 0. Next, the analysis results about the images of the respective resolutions are unified, to thereby extract the linear structure elements (blood vessels) in various sizes from the three-dimensional medical image. Then, those extracted linear structure elements are connected to each other through use of a minimum spanning tree algorithm or the like. As a result, data on a tree structure representing a tubular structure in the three-dimensional medical image is acquired. Note that, when the linear structure elements are connected to each other through use of the minimum spanning tree algorithm, a cost function based on a positional relationship between the linear structure elements and a principal axis direction of each of the linear structure elements, which is represented by an eigenvector corresponding to the eigenvalue close to 0, is used.

Further, according to the method disclosed in Japanese Patent Application Publication No. 2011-098195, a candidate region for a linear structure is extracted from a three-dimensional medical image, and from among candidate points included in the extracted candidate region for the linear structure, representative points are selected through use of graph matching so as to form a shape model that is most similar to a predetermined set shape. Then, for example, a graph structure generated based on the candidate points is corrected in such a manner as to match the graph structure with the shape model generated based on the representative points. In this manner, it is possible to generate the graph structure accurately.

SUMMARY OF INVENTION

Technical Problems

However, in the portal vein and the hepatic veins of liver, or other such structures, that branch many times and whose blood vessel branches run close to each other in such a manner as to be entangled with each other, when the blood vessel such as the portal vein is extracted by a method similar to the method described in Patent Literature 1, a branch of the hepatic veins, which is different from the portal vein, is erroneously extracted as a branch of the portal vein in some cases.

In addition, according to the method disclosed in Japanese Patent Application Publication No. 2011-098195, the graph structures of major blood vessels that are defined as the set shapes can be extracted accurately, but it is preferred that the graph structures of other portions of the blood vessels that are not defined as the set shapes, such as thin blood vessels branching from the major blood vessels, be generated without erroneously connecting branches that should not to be connected to each other.

The branches of the portal vein and pulmonary blood vessels have such a geometric feature as to repeatedly branch from a point of origin and extend in directions away from the point of origin in such a manner as to become wider, which is different from those of other blood vessels. The present invention has an object to provide an image processing apparatus, method, and program for accurately extracting, through use of this feature, a plurality of linear structures each repeatedly branching from a point of origin and extending in directions away from the point of origin in such a manner as to become wider.

Solution to Problems

According to one embodiment of the present invention, there is provided an image processing apparatus, including a graph structure generation unit configured to generate, based on medical image data including a plurality of linear structures each repeatedly branching from a point of origin and extending in directions away from the point of origin in such a manner as to become wider, graph structures by defining the plurality of linear structures through use of a plurality of nodes and a plurality of edges connecting the plurality of nodes to each other. The graph structure generation unit includes: a node extraction unit configured to extract, based on the medical image data, the plurality of nodes for defining the plurality of linear structures; a root node extraction unit configured to extract, from the extracted plurality of nodes, a plurality of root nodes corresponding respectively to the points of origin of the plurality of linear structures; a path detection unit configured to generate a path detection-use graph structure based on the plurality of nodes and detect a path that is included in the generated path detection-use graph structure and connects the plurality of root nodes to each other; and a cost setting unit configured to set, based on a predetermined condition representing a feature of an erroneous connection edge, which erroneously connects two nodes that are to belong to different graph structures to each other, the connection cost for each of edges forming the path so that the erroneous connection edge is hard to connect. The graph structure generation unit generates, based on the plurality of nodes and the set connection costs, a plurality of graph structures corresponding respectively to the plurality of linear structures.

According to one embodiment of the present invention, there is provided an image processing method for use in the above-mentioned image processing apparatus, including: a graph structure generation step of generating, based on medical image data including a plurality of linear structures each repeatedly branching from a point of origin and extending in directions away from the point of origin in such a manner as to become wider, graph structures by defining the plurality of linear structures through use of a plurality of nodes and a plurality of edges connecting the plurality of nodes to each other. The graph structure generation step includes: a node extraction step of extracting, based on the medical image data, the plurality of nodes for defining the plurality of linear structures; a root node extraction step of extracting, from the extracted plurality of nodes, a plurality of root nodes corresponding respectively to the points of origin of the plurality of linear structures; a path detection step of generating a path detection-use graph structure based on the plurality of nodes and detect a path that is included in the generated path detection-use graph structure and connects the plurality of root nodes to each other; and a cost setting step of setting, based on a predetermined condition representing a feature of an erroneous connection edge, which erroneously connects two nodes that are to belong to different graph structures to each other, a connection cost for each of edges forming the path so that the erroneous connection edge is hard to connect. The graph structure generation step includes generating, based on the plurality of nodes and the set connection costs, a plurality of graph structures corresponding respectively to the plurality of linear structures.

According to one embodiment of the present invention, there is provided an image processing program for causing a computer to execute the above-mentioned method.

Herein, the above-mentioned "linear structure" may be any structure as long as the linear structure is an object from which a shape model can be formed as the graph structure through use of the nodes and the edges connecting the nodes to each other and is a structure having such a feature as to repeatedly branch from a point of origin and extending in directions away from the point of origin in such a manner as to become wider. For example, the "linear structure" may be the blood vessel of lung or liver. Conceivable examples of the "linear structure" include pulmonary arteries and pulmonary veins of the lung and a portal vein, arteries, and hepatic veins of the liver.

Further, the medical image data may be, for example, medical image data imaged by CT, MR, ultrasonic, PET-CT, SPECT, 4D-CT, OCT, or X-ray radiography (CR, DR) apparatus. For example, the medical image data may be three-dimensional image data such as volume data.

In the image processing apparatus according to one embodiment of the present invention, in order to "generate the plurality of graph structure," the graph structure generation unit can use an arbitrary graph structure generation method as long as the method is capable of generating the graph structures based on the set connection costs so that the erroneous connection edge is hard to connect. For example, it is preferred that the graph structure generation unit generate provisional graph structures corresponding to the plurality of linear structures based on the plurality of nodes, discriminate, for each path connecting two root nodes to each other, the erroneous connection edge included in the provisional graph structures based on the set connection costs, and disconnect the discriminated erroneous connection edge, to thereby generate the plurality of graph structures from the provisional graph structures. Further, the graph structure generation unit may use other connection costs that are based on an additional viewpoint in combination with the set connection costs.

In one embodiment of the present invention, in order to "generate a path detection-use graph structure," an arbitrary method capable of extracting the path connecting the two root nodes to each other can be used. For example, the path detection-use graph structure may be a tree structure having one of the plurality of root nodes as a starting point. In this case, the following method is conceivable. Specifically, an arbitrary algorithm for generating the tree structure from one root node such as the Dijkstra's algorithm is applied so as to generate the path detection-use tree structure while setting an arbitrary one of the plurality of root nodes as its starting point, and from among the paths included in the path detection-use tree structure, a path including the root node set as the starting point and the root node different from the root node set as the starting point is extracted as the path.

In the image processing apparatus according to one embodiment of the present invention, it is preferred that the path be a shortest path connecting two root nodes that are selected from among the plurality of root nodes to each other.

Note that, in the image processing apparatus according to one embodiment of the present invention, the cost setting unit may set the connection cost for each of the edges based on an arbitrary condition as long as the condition to be used represents the feature of the erroneous connection edge erroneously connecting nodes that correspond respectively to different linear structures to each other. For example, it is preferred that the cost setting unit set the connection cost for the each of the edges forming the path so that the each of the edges is hard to connect as a distance from the two root nodes becomes larger.

In order to set the connection cost so that "the each of the edges is hard to connect as a distance from the two root nodes becomes larger" as described above, an arbitrary cost setting method for setting the cost so that the edge is hard to connect as the distance from the two root nodes becomes larger can be used. For example, the cost may be set so that the set cost is linearly proportional to the sum of distances between the two root nodes and the edge. Alternatively, the cost may be set so that the set cost takes a predetermined value in a stepwise manner for each predetermined range of the sum of the distances between the two root nodes and the edge. Further, the distance between each of the root nodes and the edge can be defined in an arbitrary manner as a distance between a point that can represent the position of the edge and the root node. For example, a distance between one of the end points of the edge (or midpoint of the edge) and the root node can be defined as the distance between the root node and the edge. Further, the representative point of the edge (point to be used to calculate the distance between each of the root nodes and the edge) may be made different for each of the two nodes.

Further, the cost setting unit may acquire, based on the medical image data, thickness of each of the linear structures corresponding to the each of the edges forming the path, and set the connection cost for the each of the edges forming the path so that the each of the edges is hard to connect as the thickness corresponding to the each of the edges becomes smaller.

In order to set the connection cost so that "the each of the edges is hard to connect as the thickness corresponding to the each of the edges becomes smaller" as described above, an arbitrary cost setting method for setting the cost so that the edge is hard to connect as the thickness corresponding to the edge becomes smaller can be used. For example, the cost may be set so that the set cost is linearly proportional to the thickness of the edge, or the cost may be set so that the set cost takes a predetermined value in a stepwise manner for each predetermined range of the thickness of the edge. In addition, an arbitrary value that represents the thickness of the linear structure corresponding to the edge can be used as the thickness corresponding to the edge. For example, an average of the values of the thickness of the linear structure corresponding to the edge can be used.

Further, the cost setting unit may set the connection cost for the each of the edges forming the path so that the each of the edges is hard to connect as an angle formed by two directional vectors directed from the each of the edges toward the respective two root nodes becomes smaller.

In order to set the connection cost so that "the each of the edges is hard to connect as an angle formed by two directional vectors directed from the each of the edges toward the respective two root nodes becomes smaller" as described above, an arbitrary cost setting method for setting the cost so that the edge is hard to connect as the angle formed by two directional vectors directed from the edge toward the respective two root nodes becomes smaller can be used. For example, the cost may be set so that the set cost is linearly proportional to an inner product of the two directional vectors directed from the edge toward the respective two root nodes. Alternatively, the cost may be set so that the set cost takes a predetermined value in a stepwise manner for each predetermined range of the value of the inner product of the two directional vectors directed from the edge toward the respective two root nodes. Further, the "two directional vectors directed from the edge toward the respective two root nodes" include not only two directional vectors linearly directed from the edge (arbitrary point that represents the edge) toward the respective two root nodes, but also two directional vectors directed from the edge (arbitrary point that represents the edge) toward a predetermined point on the path that is located further on one root node side than the edge and toward a predetermined point on this path that is located further on the other root node side than the edge, respectively.

In the image processing apparatus, the plurality of root nodes may be extracted by an arbitrary method. For example, the point of origin of the linear structure may be specified on a display screen through the user's manual operation using an input device such as a mouse, and based on coordinates specified through the operation, the node corresponding to the coordinate values may be identified as the root node of the linear structure. Alternatively, the plurality of root nodes may be extracted and identified automatically by various methods. For example, it is preferred that in order to detect the root nodes, the root node extraction unit use graph matching to compare predetermined shapes representing the plurality of linear structures with the provisional graph structures, to thereby detect the plurality of root nodes from the plurality of nodes.

Advantageous Effects of Invention

According to the image processing apparatus, method, and program of the one embodiment of the present invention, the path detection-use graph structure is generated based on the plurality of nodes representing the plurality of linear structures, and the path that is included in the generated path detection-use graph structure and connects the plurality of root nodes representing the points of origin of the plurality of linear structures to each other is detected. Then, based on the predetermined condition representing the feature of the erroneous connection edge erroneously connecting two nodes that are to belong to different graph structures to each other, the connection cost is set for each of the edges forming the path so that the erroneous connection edge is hard to connect, and based on the set connection costs, the plurality of graph structures corresponding respectively to the plurality of linear structures are generated. Accordingly, through use of such a feature that the erroneous connection edge is included in the edges forming the path connecting the plurality of root nodes to each other when the path detection-use graph structure is generated and the predetermined condition representing the additional feature of the erroneous connection edge that erroneously connects the nodes corresponding respectively to the different linear structures to each other, it is possible to generate the plurality of graph structures while suppressing the connection of the erroneous connection edge. Accordingly, the erroneous connection of the respective nodes can be suppressed even in a portion in which the plurality of structures are close to each other, and hence the plurality of graph structures can be generated efficiently and accurately.

DESCRIPTION OF EMBODIMENT

Figure 1:
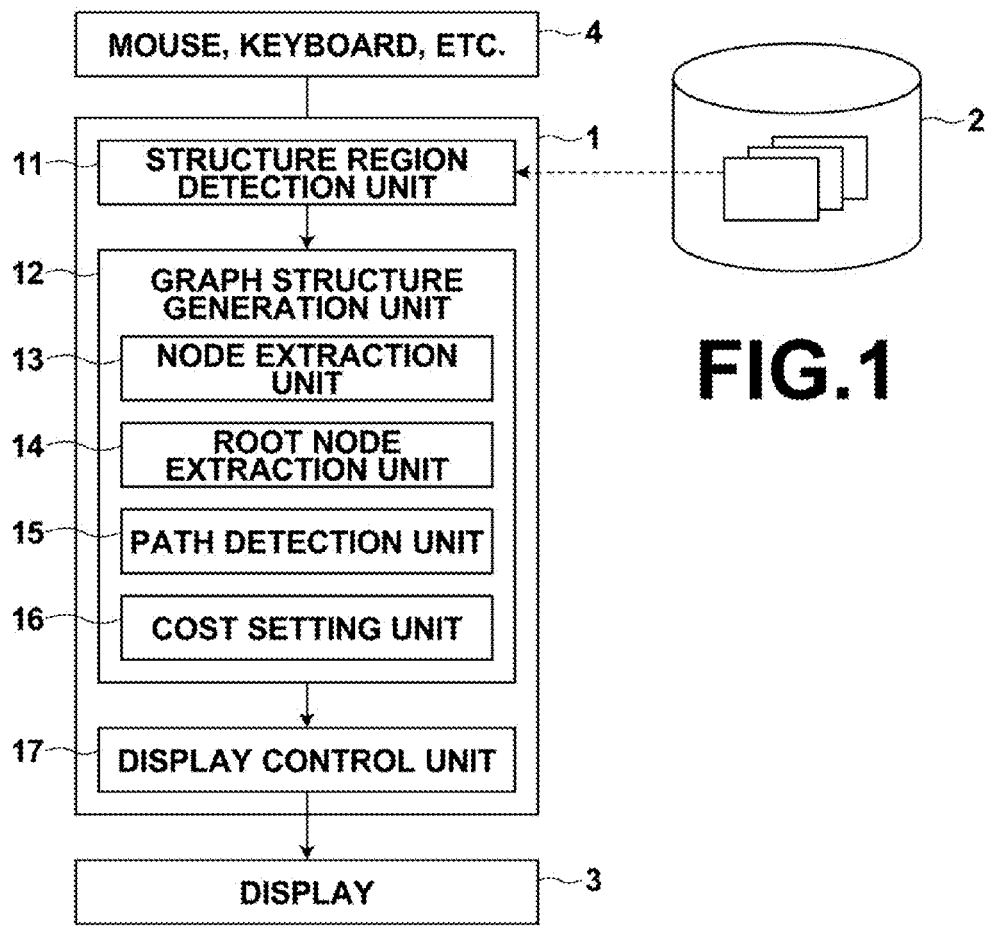
FIG. 1 is a functional block diagram of an image processing apparatus according to one embodiment of the present invention.

Now, an image processing apparatus according to an embodiment of the present invention is described in detail with reference to the drawings. FIG. 1 is a schematic configuration diagram of an image processing apparatus 1 according to a first embodiment of the present invention. The image processing apparatus 1 is configured to generate, from medical image data including a plurality of linear structures each repeatedly branching from a point of origin and extending in directions away from the point of origin in such a manner as to become wider, a plurality of graph structures corresponding respectively to the plurality of linear structures. Note that, the configuration of the image processing apparatus 1 such as the one illustrated in FIG. 1 is implemented by executing, on a computer, an image processing program read into an auxiliary storage device. In this case, the image processing program is stored in a storage medium such as a CD-ROM, or distributed via a network such as the Internet, to be installed onto a computer. The image processing apparatus 1 of FIG. 1 generates, from pieces of image data representing linear structures such as a portal vein and veins of liver, graph structures representing the portal vein (first linear structure) and the veins (second linear structure), respectively. The image processing apparatus 1 includes a structure region detection unit 11, a graph structure generation unit 12, and a display control unit 17. Further, the graph structure generation unit 12 includes a node extraction unit 13, a root node extraction unit 14, a path detection unit 15, and a cost setting unit 16. Moreover, the computer in this embodiment having the image processing program installed thereon includes a main body to function as the image processing apparatus 1, a display device 3 formed of a display, an input device 4 such as a mouse and keyboard, and a storage unit 2 formed of a memory, a hard disk, and the like.

Figure 2:
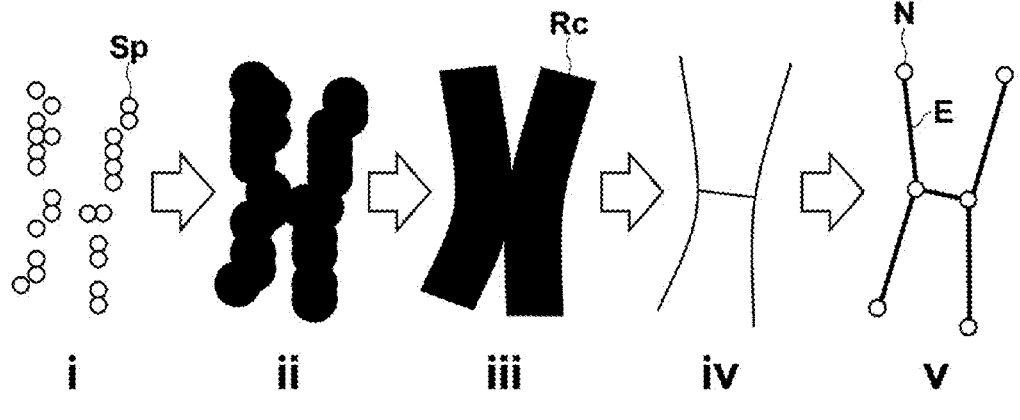
FIG. 2 is a diagram illustrating processing of generating provisional graph structures representing a portal vein and hepatic veins of liver according to one embodiment of the present invention.

FIG. 2 is a schematic diagram illustrating how a blood vessel, which is a region representing the portal vein or the hepatic veins, is extracted as a candidate region $R^c$ for the blood vessel and the candidate region is formed into a graph based on the extracted blood vessel region to extract a provisional graph structure. A description is given of, by taking the portal vein (first linear structure) and the hepatic veins (second linear structure) of the liver as an example, a case where the candidate regions $R_c$ for the portal vein and the hepatic veins are detected from volume data. Note that, image data is formed of a two-dimensional image that is stored in the storage unit 2 and has been imaged by an imaging apparatus or a radiation detection apparatus, for example, or three-dimensional volume data that is generated from a plurality of two dimensional images.

The structure region detection unit 11 is configured to determine whether or not a given region in the image data constitutes a part of the portal vein or the hepatic veins, to thereby detect the given region as the candidate region $R^c$. FIG. 2 is a diagram illustrating structure detection processing according to this embodiment. As illustrated in part i of FIG. 2, based on values of voxel data forming the volume data, the structure region detection unit 11 obtains, through statistics or the like, the value of the voxel data that is already known to be a pixel representing the portal vein, and uses the value of the voxel data to extract a pixel that is likely to be the portal vein or the hepatic veins as a candidate point. The structure region detection unit 11 then calculates the positions of a plurality of candidate points Sp forming core lines of the portal vein or hepatic veins. As illustrated in part ii of FIG. 2, the structure region detection unit 11 expands the candidate points Sp (p=1 to n: n is the number of candidate points extracted). Further, as illustrated in part iii of FIG. 2, the structure region detection unit 11 determines, as a portal vein region or a hepatic vein region, image data that has a predetermined range of pixel values, which includes pixel values of the expanded candidate points Sp that represent the portal vein or the hepatic veins, and extracts the image data as the candidate region $R^c$.

Note that, the method to be applied by the structure region detection unit 11 is not limited to that of this embodiment, and may apply various well-known methods capable of extracting the candidate region $R^c$. For example, the structure region detection unit 11 may calculate a feature amount of the voxel data around the candidate point that indicates how likely the voxel data is the portal vein (or how likely the voxel data is the hepatic veins), and based on the calculated feature amount, determine whether or not the voxel data represents the portal vein region (or the hepatic vein region). In this case, it is conceivable that the determination based on the feature amount is made based on an evaluation function that is acquired in advance through machine learning. Alternatively, the structure region detection unit 11 may detect the candidate region by one of the methods disclosed in JP 2010-200925 A and Patent Literature 1, or another publicly-known method.

The graph structure generation unit 12 is configured to generate, based on the medical image data including the plurality of linear structures each repeatedly branching from a point of origin and extending in directions away from the point of origin in such a manner as to become wider, the graph structures by defining the plurality of linear structures through use of a plurality of nodes and a plurality of edges connecting the nodes to each other.

In this embodiment, the graph structure generation unit 12 acquires the candidate region such as the one illustrated in part iii of FIG. 2, which is detected by the structure region detection unit 11 based on the medical image data, thins the acquired candidate region $R_c$ by a well-known method as illustrated in part iv of FIG. 2, and divides lines obtained by the thinning processing at branching points as illustrated in part v of FIG. 2. The graph structure generation unit 12 then defines the branching points and end points as a plurality of nodes and defines the divided line segments as a plurality of edges, to thereby extract provisional graph structures representing the portal vein and the hepatic veins. Note that, the graph structure generation unit 12 may divide the lines obtained by the thinning processing not only at the branching points, but also under a predetermined condition such as at predetermined intervals, in order to enable a gently-curved portion of the lines obtained by the thinning processing to be divided as appropriate into a plurality of line segments along the curve.

Note that, as the method of extracting the provisional graph structures representing the first and second linear structures from the image data, any well-known method is applicable other than the above-mentioned method as long as the method is capable of extracting the linear structure as a candidate for the graph structure defined through use of the plurality of nodes and the plurality of edges.

The graph structure generation unit 12 includes the node extraction unit 13. The node extraction unit 13 is configured to extract the plurality of nodes, which are defined by the above-mentioned processing of generating the provisional graph structures, as the plurality of nodes for defining the plurality of linear structures. The node extraction unit 13 may extract the plurality of nodes by an arbitrary method as long as the method is capable of extracting the plurality of nodes for defining the plurality of linear structures.

The graph structure generation unit 12 includes the root node extraction unit 14. The root node extraction unit 14 is configured to extract, from the candidate points Sp, a plurality of root nodes corresponding respectively to points of origin of the plurality of linear structures. The root node extraction unit 14 in this case extracts root nodes $NA_0$ and $NB_0$ corresponding respectively to the points of origin of the portal vein and the hepatic veins. Moreover, the root node extraction unit 14 in this embodiment uses graph matching to compare known model shapes (predetermined shapes) representing the portal vein and the hepatic veins that are the plurality of linear structures with the provisional graph structures representing the portal vein and the hepatic veins, which are described in detail later, as disclosed in Patent Literature 2. In this manner, the root node extraction unit 14 detects the plurality of root nodes from the plurality of candidate points.

Figure 3:
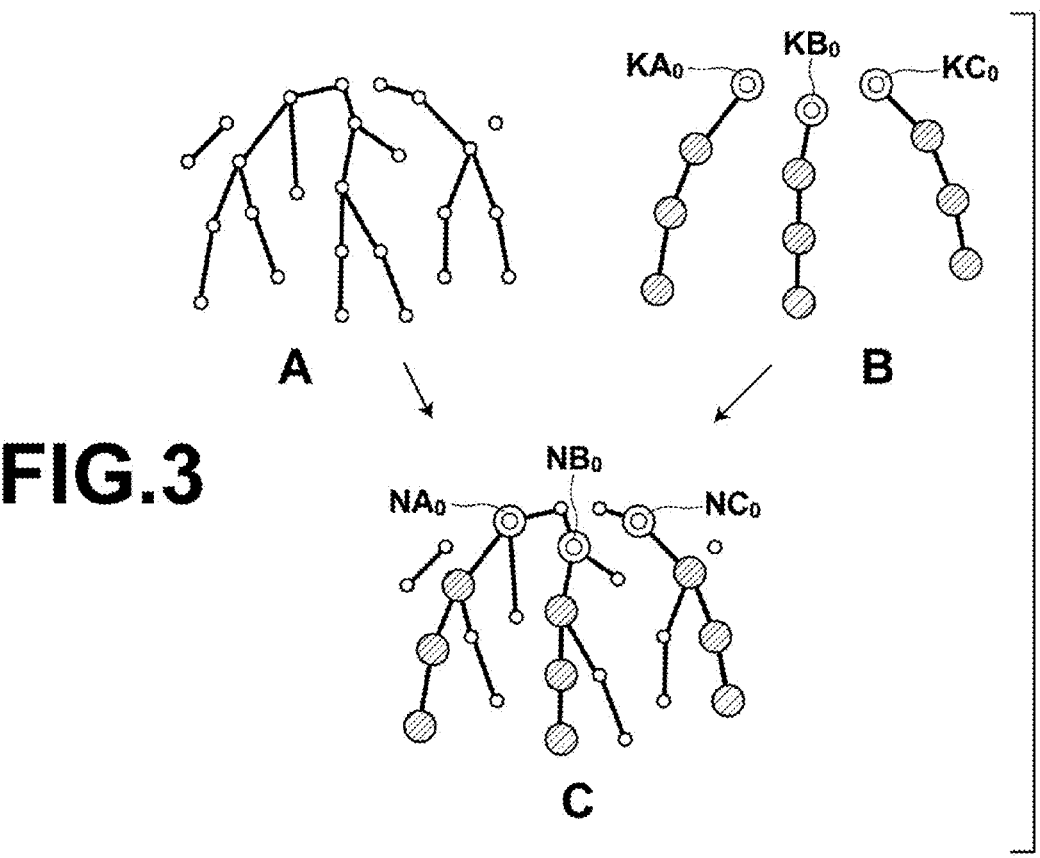
FIG. 3 is a diagram illustrating root node detection processing according to one embodiment of the present invention.

FIG. 3 is a conceptual diagram illustrating a method of extracting the root nodes $NA_0$ and $NB_0$ from the plurality of candidate points Sp through use of the graph matching. As illustrated in part C of FIG. 3, the root node extraction unit 14 performs matching between the provisional graph structures representing a plurality of structures (in the case of the blood vessels of the liver, for example, the portal vein, two hepatic veins, and the like), which are illustrated in part A of FIG. 3, and model shapes that are generated in advance by a well-known method and represent the portal vein and the two hepatic veins, which are illustrated in part B of FIG. 3. The root node extraction unit 14 then extracts nodes of the provisional graph structures that are located in positions corresponding to points of origins $KA_0$, $KB_0$, and $KC_0$ of the model shapes illustrated in part B of FIG. 3 as root nodes $NA_0$, $NB_0$, and $NC_0$, respectively.

Note that, the root node extraction unit 14 may use an arbitrary method as long as the method is capable of extracting the plurality of root nodes corresponding respectively to the point of origins of the plurality of linear structures.

The graph structure generation unit 12 includes the path detection unit 15. The path detection unit 15 is configured to generate a path detection-use graph structure based on the plurality of nodes extracted and detect a path connecting the plurality of root nodes included in the generated path detection-use graph structure to each other. The respective root nodes belong to the different graph structures, and hence it is conceivable that the path connecting at least two root nodes to each other includes an erroneous connection edge. The graph structure generation unit 12 therefore uses the paths connecting at least two root nodes to each other to detect the erroneous connection edge as described later.

In this embodiment, the path detection unit 15 uses the nodes and edges of the provisional graph structures to generate a tree structure (path detection-use graph structure) for detecting a path having the root node $NA_0$, which is one of the plurality of root nodes, as its starting point through use of the Dijkstra's algorithm. The path detection unit 15 then extracts, from among the paths included in the tree structure for detecting the path, a path including the root node $NA_0$ set as the starting point and the root node $NB_0$, which is different from the root node $NA_0$ set as the starting point. Note that, in the case where the tree structure for detecting the path is generated as in this embodiment, an arbitrary algorithm capable of generating the tree structure such as a shortest path tree or a minimum spanning tree is applicable.

Further, when a plurality of paths are extracted as the paths connecting the two root nodes $NA_0$ and $NB_0$ to each other, the path detection unit 15 extracts the shortest path connecting the two root nodes $NA_0$ and $NB_0$ to each other. Note that, as long as it can be considered that a feature of the erroneous connection edge described later (such a feature that a possibility that the nodes erroneously connected to each other by the erroneous connection edge are detected at positions away from the plurality of root nodes is sufficiently high) is maintained, the path detection unit 15 may detect, as the path, a path connecting the two root nodes $NA_0$ and $NB_0$ to each other that is different from the shortest path. For example, the path detection unit 15 may detect, in place of the shortest path connecting the two root nodes $NA_0$ and $NB_0$ to each other, the second or third shortest path connecting the two root nodes $NA_0$ and $NB_0$ to each other.

The path detection unit 15 is not limited to that of this embodiment, and another method capable of detecting the path connecting the plurality of root nodes to each other may be used as the path detection unit 15. For example, the path detection unit 15 may use the provisional graph structure as the path detection-use graph structure to detect the path including the plurality of root nodes as follows. First, the path detection unit 15 attaches an identification label to one of the root nodes included in the provisional graph structure, attaches the identification label to another node connected to the root node to which the identification label is attached, attaches the identification label to still another node connected to the node to which the identification label is attached, and in the same manner sequentially, performs labeling by attaching the identification labels to the nodes forming the provisional graph structure. After the labeling processing, the path detection unit 15 then detects the root node to which the identification label is attached, and when another root node different from the root node to which the identification label is attached first is detected, determines that the other root node and the root node to which the identification label is attached first is connected to each other through the path. In this case, based on the two root nodes determined as being connected to each other through the path, the path detection unit 15 can detect the path connecting those two root nodes to each other by an arbitrary method.

The graph structure generation unit 12 includes the cost setting unit 16. The graph structure generation unit 12 is configured to generate, based on connection costs set in the cost setting unit 16, the plurality of graph structures corresponding respectively to the plurality of linear structures.

The cost setting unit 16 is configured to set, based on a predetermined condition representing the feature of the erroneous connection edge, which erroneously connects two nodes that are to belong to different graph structures to each other, the connection cost for each of the edges forming the path so that the erroneous connection edge is hard to connect.

In order to set this connection cost, the present invention assumes that because the respective root nodes belong to different graph structures, the paths each connecting at least two root nodes to each other includes the erroneous connection edge, and considers the feature of the erroneous connection edge, which erroneously connects the nodes that are to belong to different graph structures to each other, among the edges forming the path each connecting the at least two root nodes to each other, as follows.

First, in a plurality of predetermined linear structures, such as the portal vein and the hepatic veins, that repeatedly branch from the point of origin and extending in the directions away from the point of origin in such a manner as to become wider, it is conceivable that the nodes that are to belong to different graph structures are likely to be close to each other at positions away from at least two of the points of origin of the plurality of linear structures, to be erroneously connected to each other. In other words, it is conceivable that each of the edges forming the paths is more likely to be the erroneous connection edge as its distance from at least two of the points of origin of the plurality of linear structures becomes larger (Feature 1).

In this case, based on Feature 1, the cost setting unit 16 acquires the paths assumed to include the erroneous connection edge, and for each of the paths, sets the connection cost for each of the edges forming the path so that the edge is hard to connect as the distance from at least two of the points of origin of the plurality of linear structures becomes larger.

Specifically, the cost setting unit 16 sets, for each of the edges forming the path connecting at least two root nodes to each other, the connection cost so that the edge is hard to connect as the sum of distances from the two root nodes becomes larger. For example, for each of the edges, when the distance between the midpoint of an edge $E_i$ and the root node $NA_0$ is represented by $LA_i$ and the distance between the midpoint of the edge $E_i$ and the root node $NB_0$ is represented by $LB_i$, the cost setting unit 16 may set, for the edge $E_i$, $LA_i+LB_i$ as the connection cost.

Note that, the cost setting unit 16 in this embodiment may use another connection cost setting method as long as the method involves setting, for each of the edges forming the path connecting at least two root nodes to each other, the connection cost so that the edge is hard to connect as the distance from the two root nodes becomes larger. Further, in this embodiment, the cost setting unit 16 sets the connection cost so that the edge is hard to connect as the connection cost becomes larger, but the present invention is not limited thereto. The cost setting unit 16 may set the connection cost so that the edge is hard to connect as the connection cost becomes smaller.

The graph structure generation unit 12 in this embodiment discriminates, based on the connection costs set in the above-mentioned manner, for each of the paths including the plurality of root nodes, the erroneous connection edge included in the provisional graph structures and disconnects the discriminated erroneous connection edge, to thereby generate, from the provisional graph structures, a first graph structure corresponding to the portal vein and a second graph structure corresponding to the hepatic veins (plurality of graph structures).

The display control unit 17 is configured to appropriately display the provisional graph structures generated by the graph structure generation unit 12, the plurality of graph structures that are finally acquired, and the like on the display as needed.

Figure 4A:
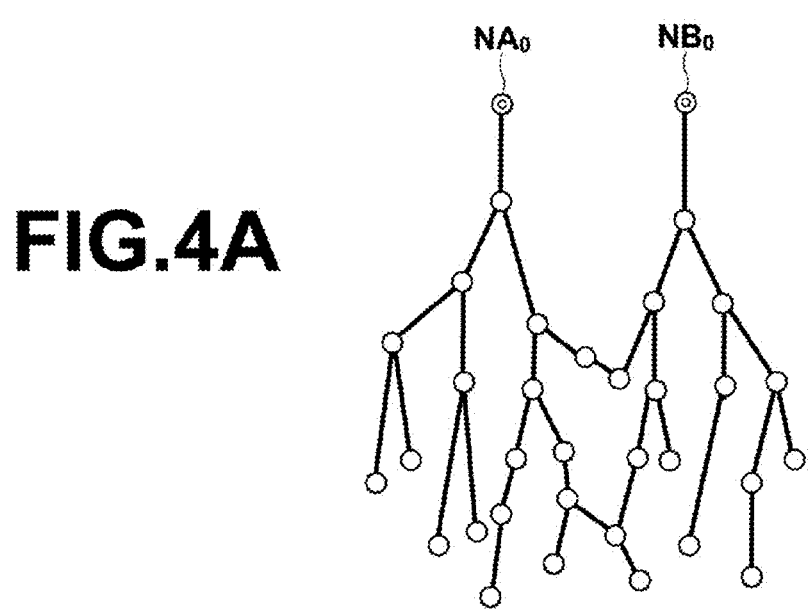
FIG. 4A is a diagram illustrating a graph structure generation method according to one embodiment of the present invention (Part 1).

FIG. 4A to FIG. 4D are diagrams illustrating a method of generating, based on the costs calculated by the above-mentioned cost function from the provisional graph structures, the first graph structure corresponding to the portal vein and the second graph structure corresponding to the hepatic veins. Further, FIG. 5 is a flow chart illustrating a flow of image processing according to this embodiment. Referring to FIG. 4A to FIG. 5, the flow of the image processing according to this embodiment is described.

First, the structure region detection unit 11 extracts the plurality of candidate points Sp from the medical image data in the above-mentioned manner (S01). The structure region detection unit 11 then extracts the candidate region $R_c$ based on the plurality of candidate points Sp (S02). The graph structure generation unit 12 next thins the candidate region $R_c$ to generate the provisional graph structures through use of the edge and the nodes as illustrated in FIG. 4A (S03). Note that, FIG. 4A is an image diagram illustrating the provisional graph structures respectively representing the portal vein and the hepatic veins, which are extracted by the graph structure generation unit 12. As illustrated in FIG. 4A, when the plurality of linear structures, such as the portal vein and the hepatic veins, that extend close to each other in such a manner as to be entangled with each other are extracted as the candidates for the graph structures by a well-known method, there has been a problem in that in the candidates for the graph structures, in a portion in which the plurality of linear structures are very close to each other, the node of the graph structure representing one linear structure is erroneously connected to the graph structure representing another linear structure. In other words, as illustrated in FIG. 4A, there has arisen a problem in that the node of the graph structure representing the hepatic veins and the node of the graph structure representing the portal vein, which are not supposed to be connected to each other, are erroneously connected to each other by an edge.

Subsequently, the root node extraction unit 14 performs matching between the provisional graph structures and the model shapes representing the portal vein and the hepatic veins through the graph matching to detect, as the plurality of root nodes, the nodes of the provisional graph structures that are located in the positions corresponding to the points of origin of the model shapes representing the portal vein and the hepatic veins (S04).

Subsequently, the path detection unit 15 uses the nodes and edges forming the provisional graph structures to generate a path detection-use tree structure having the first root node NA) as its starting point. When the paths forming the path detection-use tree structure include a path including the two root nodes $NA_0$ and $NB_0$, the path detection unit 15 then detects the shortest path from among the paths each including the two root nodes $NA_0$ and $NB_0$ (S05, YES). On the provisional graph structures illustrated in FIG. 4B, the detected path is indicated by the thick line.

Subsequently, the cost setting unit 16 sets the connection cost for each of the edges forming the detected path (thick line of FIG. 4B). Specifically, the cost setting unit 16 sets, as the connection cost, for the i-th edge $E_i$ ($0 \le i \le q$, q represents the number of edges) from the root node $NA_0$ side, the sum $LA_i+LB_i$ of the distance from a node $NA_i$ located on a predetermined side of the edge $E_i$ to the root node $NA_0$ and the distance from the node $NA_i$ to the root node $NB_0$ (S06).

Figure 4B:
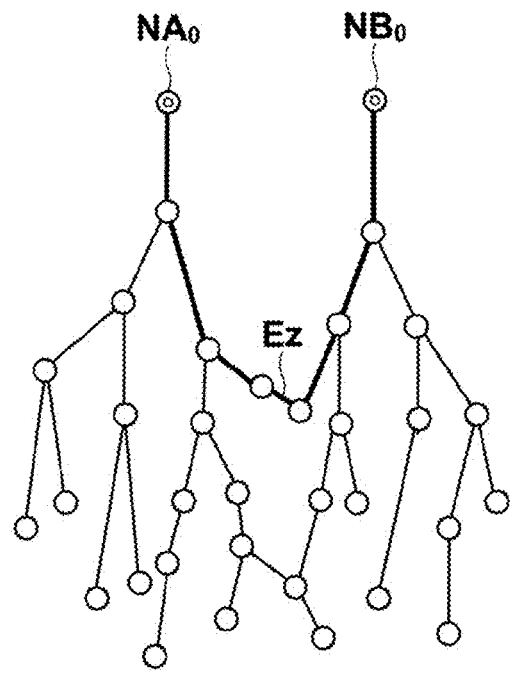
FIG. 4B is a diagram illustrating the graph structure generation method according to one embodiment of the present invention (Part 2).
Figure 5:
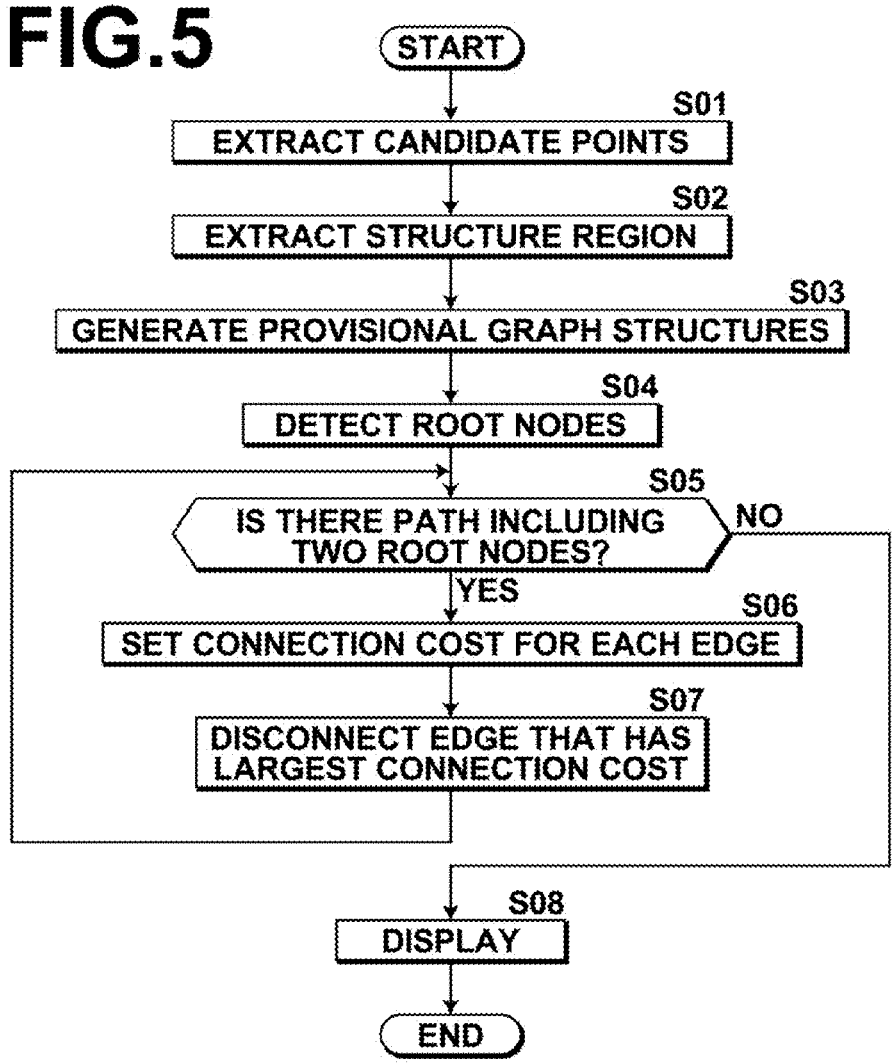
FIG. 5 is a flow chart illustrating a flow of processing of an image processing method according to one embodiment of the present invention.

Next, the graph structure generation unit 12 compares the connection costs of the respective edges on the path including the two root nodes $NA_0$ and $NB_0$ with one another, and disconnects the edge Ez illustrated in FIG. 4B that has the largest connection cost (S07).

Figure 4C:
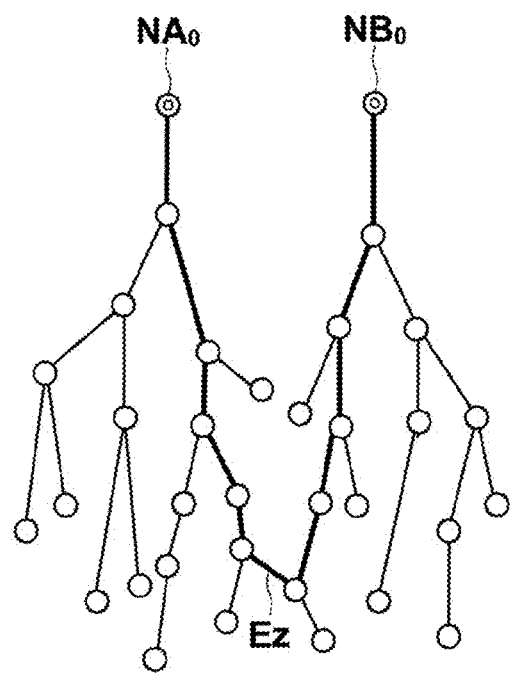
FIG. 4C is a diagram illustrating the graph structure generation method according to one embodiment of the present invention (Part 3).

Then, the path detection unit 15 confirms whether there is another path including the two root nodes $NA_0$ and $NB_0$ in the path detection-use tree structure having the root node $NA_0$ as its starting point. When there is another path including the two root nodes $NA_0$ and $NB_0$ (S05, YES), the path detection unit 15 detects the shortest path including the two root nodes $NA_0$ and $NB_0$, and the processing of Steps S06 and S07 is repeated. In other words, as illustrated in FIG. 4C, the path detection unit 15 detects the shortest path including the root nodes $NA_0$ and $NB_0$ of the first and second graph structures (thick line of FIG. 4C) (S05). The cost setting unit 16 then sets, as the connection cost, for the i-th edge $E_i$ from the root node $NA_0$ side that is included in the path, the sum $LA_i+LB_i$ of the distance from the node $NA_i$ located on the predetermined side of the edge $E_i$ to the root node $NA_0$ and the distance from the node $NA_i$ to the root node $NB_0$ in the same manner as described above (S06). The graph structure generation unit 12 next compares the connection costs of the respective edges with one another, and disconnects the edge Ez that has the largest connection cost from among the edges of FIG. 4C (S07).

Figure 4D:
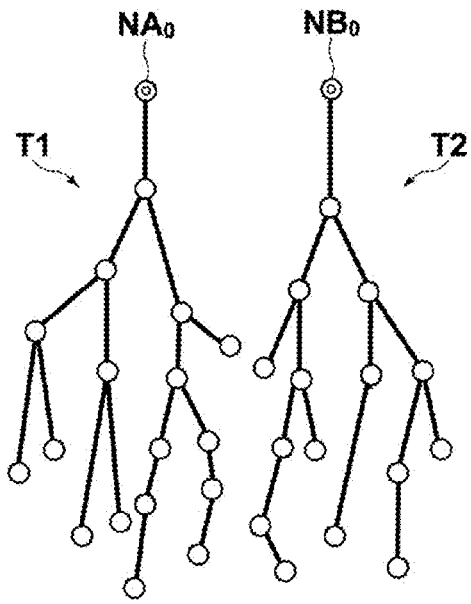
FIG. 4D is a diagram illustrating the graph structure generation method according to one embodiment of the present invention (Part 4).
Figure 7:
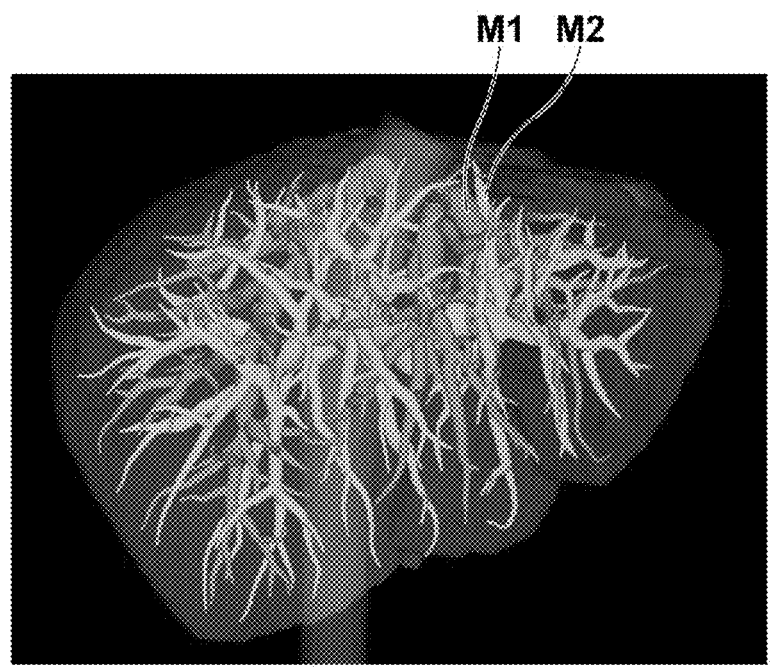
FIG. 7 is an image diagram illustrating a portal vein and hepatic veins of liver, which are displayed based on first and second graph structures generated by the image processing method according to one embodiment of the present invention.

On the other hand, when it is confirmed that there is no path including the two root nodes $NA_0$ and $NB_0$ in the shortest path tree having the root node $NA_0$ as its starting point (S05, NO), all the plurality of root nodes $NA_0$ and $NB_0$ belong to different graph structures as illustrated in FIG. 4D, and hence the generation of a plurality of graph structures T1 and T2 corresponding respectively to the plurality of linear structures is completed. The display control unit 17 displays the plurality of graph structures as necessary (S08). FIG. 7 is an image diagram illustrating a portal vein M1 and hepatic veins M2, which are extracted based on the plurality of graph structures T1 and T2 that have been generated by the above-mentioned processing. As illustrated in FIG. 7, the display control unit 17 controls the display 3 to display the portal vein M1 and the hepatic veins M2 by a well-known method based on the graph structures T1 and T2 that have been generated by the graph structure generation unit 12.

Note that, when three or more root nodes are extracted from the medical image data, in Step S05, the path detection unit 15 selects one root node in order from among the plurality of root nodes and generates the shortest path tree while setting the selected root node as its starting point, to confirm whether or not there is a path including other root nodes different from the root node set as the starting point. Then, when there is any path including the other two root nodes (S05, YES), the path detection unit 15 detects the shortest path and the processing of Steps S06 and S07 is repeated. Meanwhile, when it is confirmed that even if the shortest path tree is generated with every root node being set as the starting point, there is no path including the other root nodes (S05, NO), the plurality of graph structures are displayed as necessary and the processing is brought to an end (S08).

As described above, according to this embodiment, the path detection-use graph structure is generated based on the plurality of nodes representing the plurality of linear structures, and the path that is included in the generated path detection-use graph structure and connects the plurality of root nodes representing the points of origin of the plurality of linear structures to each other is detected. Then, based on the predetermined condition representing the feature of the erroneous connection edge erroneously connecting two nodes that are to belong to different graph structures to each other, the connection cost is set for each of the edges forming the path so that the erroneous connection edge is hard to connect, and based on the set connection costs, the plurality of graph structures corresponding respectively to the plurality of linear structures are generated. Accordingly, through use of such a feature that the erroneous connection edge is included in the edges forming the path connecting the plurality of root nodes to each other when the path detection-use graph structure is generated and the predetermined condition representing the additional feature of the erroneous connection edge that erroneously connects the nodes corresponding respectively to the different linear structures to each other, it is possible to generate the graph structure while suppressing the connection of the erroneous connection edge. Accordingly, even in the portal vein and the hepatic veins of the liver or other such structures that branch many times and whose blood vessel branches run close to each other in such a manner as to be entangled with each other, the erroneous connection of the respective nodes can be suppressed even in a portion in which the plurality of structures are close to each other, and hence the plurality of graph structures can be generated efficiently and accurately.

Further, it is conceivable that the path connecting the two root nodes to each other clearly shows a feature representing relative positions of the erroneous connection edge and the root nodes in the path including the erroneous connection edge and a feature representing the shape of the structure such as the thickness thereof, as in Feature 1 described above and Features 2 and 3 to be described later. Accordingly, as in the embodiment described above, by the graph structure generation unit 12 generating the provisional graph structures corresponding to the plurality of linear structures based on the plurality of nodes, discriminating the erroneous connection edge based on the set connection costs for each of the paths connecting the two root nodes to each other, and disconnecting the discriminated erroneous connection edge, the feature representing the shape of the structure and the feature representing the relative positions of the erroneous connection edge and the root nodes in the path including the erroneous connection edge can be easily and suitably reflected in the connection costs. Accordingly, the erroneous connection edge can be discriminated accurately to be disconnected.

Note that, the cost setting unit 16 weights, based on Feature 1, the edge so that the edge is hard to connect as the distance from the edge to the root nodes becomes larger, and hence how likely the edge is the erroneous connection edge can be easily and suitably evaluated.

Note that, the cost setting unit 16 may set the connection cost for each of the edges based on an arbitrary condition as long as the condition to be used represents the feature of the erroneous connection edge, which erroneously connects nodes that are to belong to different linear structures to each other.

For example, if Feature 1 is seen from another viewpoint, it is conceivable that at a position away from at least two of the points of origin of the plurality of linear structures, an angle formed by vectors directed from this position toward the at least two of the points of origin of the plurality of linear structures is small. It is therefore conceivable that as an angle formed by vectors directed from a point that represents each of the edges forming the path connecting at least two root nodes to each other toward the at least two of the points of origin of the plurality of linear structures becomes smaller, the edge is more likely to be the erroneous connection edge (Feature 2).

The cost setting unit 16 may set, based on Feature 2, the connection cost for each of the edges forming the path connecting at least two root nodes to each other so that the edge is hard to connect as an angle formed by two directional vectors directed from the edge toward the respective two root nodes becomes smaller. In this case, the cost setting unit 16 can use an arbitrary cost setting method for setting the cost so that the edge is hard to connect as the angle formed by two directional vectors directed from the edge toward the respective two root nodes becomes smaller. Further, the cost setting unit 16 may calculate the angle formed by two directional vectors directed from the edge toward the respective root nodes based on an arbitrary point that represents each of the edges.

Figure 6:
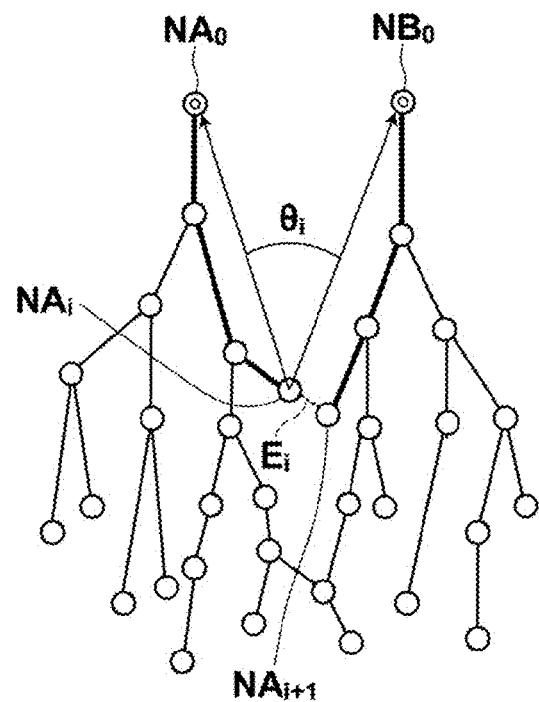
FIG. 6 is a diagram illustrating a method of setting a cost between each pair of nodes according to one embodiment of the present invention.

FIG. 6 is a diagram illustrating a method of setting the connection cost based on the angle. For example, as illustrated in FIG. 6, the cost setting unit 16 can set, for the i-th edge $E_i$ (0≤i≤q, q represents the number of edges) from the root node $NA_0$ that forms the path connecting at least two root nodes to each other, a value f defined by Expression (1) as the connection cost. Expression (1) expresses an angle $\theta_i$ formed by two directional vectors directed from the node $NA_i$ on the root node $NA_0$ side toward the respective two root nodes $NA_0$ and $NB_0$ in the form of an inner product. Accordingly, through use of the value 11 defined by Expression (1) as the connection cost, the cost setting unit 16 can set the connection cost so that the edge is hard to connect as the angle $\theta_i$ becomes smaller. Also in this case, the cost setting unit 16 can easily and suitably evaluate how likely the edge is the erroneous connection edge.

[Math. 1]

$$f_i = \frac{\overrightarrow{NA_iNA_0} \cdot \overrightarrow{NA_iNB_0}}{|\overrightarrow{NA_iNA_0}||\overrightarrow{NA_iNB_0}|} \quad (1)$$

Further, the "two directional vectors directed from the edge toward the respective two root nodes" include not only two directional vectors linearly directed from an arbitrary point that represents the edge $E_i$ in the directions of the respective two root nodes $NA_0$ and $NB_0$, but also two directional vectors directed from the arbitrary point that represents the edge $E_i$ toward a predetermined point that is located on the root node $NA_0$ side on a path connecting the two root nodes $NA_0$ and $NB_0$ to each other and toward a predetermined point that is located on the root node $NB_0$ side on this path, respectively. For example, the cost may be set based on an angle formed by a vector directed from the point $NA_i$ representing the edge $E_i$ toward a node $NA_{i-p}$, which is a p-th node (0<p<i) from the point $NA_i$ that is located on one root node $NA_0$ side, and a vector directed from the point $NA_i$ representing the edge $E_i$ toward a node $NA_{i+p}$, which is a p-th node from the point $NA_i$ that is located on the other root node $NB_0$ side.

Moreover, if Feature 1 is seen from still another viewpoint, when the linear structure has such a characteristic that its thickness is smaller at a position located farther from the point of origin, it is presumed that as the thickness of a portion of the linear structure corresponding to the edge becomes smaller, this portion is located farther from the point of origin. Accordingly, when the linear structure has such a characteristic that its thickness is smaller at a position located farther from the point of origin, it is conceivable that each of the edges forming the path connecting at least two root nodes to each other is more likely to be the erroneous connection edge as the thickness of a portion of the linear structure corresponding to the edge becomes smaller (Feature 3).

The cost setting unit 16 may use, based on Feature 3, structure region data extracted by the structure region detection unit to acquire the thickness of the linear structure corresponding to each of the edges forming the path connecting at least two root nodes to each other, and set the connection cost for each of the edges forming the path so that the edge is hard to connect as the thickness corresponding to the edge becomes smaller. In this case, the cost setting unit 16 can use an arbitrary cost setting method for setting the cost so that the edge is hard to connect as the thickness of the edge becomes smaller. For example, the cost setting unit 16 may set the cost so that the set cost is linearly proportional to the thickness of the edge, or set the cost so that the set cost takes a predetermined value in a stepwise manner for each predetermined range of the thickness of the edge. In addition, an arbitrary value that represents the thickness of the linear structure corresponding to the edge can be used as the thickness corresponding to the edge. For example, an average of the values of the thickness of the linear structure corresponding to the edge can be used. Note that, also in this case, the cost setting unit 16 can easily and suitably evaluate how likely a given edge is the erroneous connection edge.

Further, the cost setting unit 16 may use an arbitrary combination of the connection costs that are acquired based on Features 1 to 3 as the connection cost.

The cost setting unit 16 determines the erroneous connection edge, which connects to each other the plurality of structures repeatedly branching from the point of origin and extending in the directions away from the point of origin in such a manner as to become wider, based on at least one feature selected from among Features 1 to 3, and when the edge satisfies the feature used for the determination, sets the connection cost so that the edge is hard to connect. In this case, it is possible to easily and suitably generate the graph structure while weighting, with the features of the erroneous connection edge, how easily each of the nodes is connected to another node. Moreover, in the case where the shortest path including the plurality of root nodes is used as the path including the plurality of root nodes as in the embodiment, it is possible to discriminate the edge that is highly likely to be the erroneous connection edge more accurately based on Features 1 to 3.

Further, in the case where the tree structure having one of the plurality of root nodes as its starting point is used as the path detection-use graph structure as in this embodiment, the tree structure generation method for suitably connecting the shortest path such as the Dijkstra's algorithm is applied so as to generate the path detection-use tree structure while setting an arbitrary one of the plurality of root nodes as its starting point, and from among the paths included in the path detection-use tree structure, the path including the root node set as the starting point and the root node different from the root node set as the starting point can be extracted as the target path. It is therefore possible to suitably detect the shortest path including the erroneous connection edge.

Further, the root node extraction unit 14 uses the graph matching to compare the predetermined shapes representing the plurality of linear structures with the provisional graph structures, to thereby detect the plurality of root nodes from the plurality of nodes. It is therefore possible to reduce time and labor to set the root nodes as compared with a case where the root nodes are manually set.

Note that, in order to generate the provisional graph structure, the graph structure generation unit 12 in this embodiment can use various well-known methods of generating the graph structure based on the cost function for evaluating the cost of each node. For example, when the linear structure can be expressed in the form of the tree structure, an optimum path may be determined through a well-known spanning tree generation algorithm such as a minimum spanning tree algorithm or a shortest path tree algorithm in such a manner as to obtain max$\Sigma$f, to thereby generate the provisional graph structure.

Further, the present invention is not limited each of the embodiments described above, and an additional well-known weighting method may be arbitrarily used in combination. For example, the connection cost may be further weighted so that the strength of connection becomes higher as the distance between the nodes becomes smaller. Note that, the present invention is not limited to each of the embodiments described above, and various well-known methods of extracting the root node are applicable to the present invention.

Further, the portal vein is used as the predetermined structure in the description given above, but the predetermined structure may be any structure as long as the predetermined structure is an object from which a shape model can be formed as the graph structure through use of points and edges connecting the points to each other and has such a feature as to repeatedly branch from a point of origin and extending in directions away from the point of origin in such a manner as to become wider. For example, the predetermined structure may be the blood vessels of lung or liver. Examples of the predetermined structure further include pulmonary arteries, pulmonary veins, and a portal vein, hepatic arteries, and hepatic veins of liver. Further, the graph structure corresponding to the linear structure may be such a tree structure as exemplified in this embodiment, or may be a graph structure including a closed path (circuit).

What is claimed is:

1. An image processing apparatus, comprising a graph structure generation unit configured to generate, based on medical image data including a plurality of linear structures each repeatedly branching from a point of origin and extending in directions away from the point of origin in such a manner as to become wider, graph structures by defining the plurality of linear structures through use of a plurality of nodes and a plurality of edges connecting the plurality of nodes to each other, wherein the graph structure generation unit comprises:
 a node extraction unit configured to extract, based on the medical image data, the plurality of nodes for defining the plurality of linear structures;
 a root node extraction unit configured to extract, from the extracted plurality of nodes, a plurality of root nodes corresponding respectively to the points of origin of the plurality of linear structures;
 a path detection unit configured to generate a path detection-use graph structure based on the plurality of nodes and detect a path that is included in the generated path detection-use graph structure and connects the plurality of root nodes to each other; and
 a cost setting unit configured to set, based on a predetermined condition representing a feature of an erroneous connection edge, which erroneously connects two nodes that are to belong to different graph structures to each other, a connection cost for each of edges forming the path so that the erroneous connection edge is hard to connect, and
wherein the graph structure generation unit generates, based on the plurality of nodes and the set connection costs, a plurality of graph structures corresponding respectively to the plurality of linear structures.

2. An image processing apparatus according to claim 1, wherein the graph structure generation unit generates provisional graph structures corresponding to the plurality of linear structures based on the plurality of nodes, discriminate, for each path connecting the two root nodes to each other, the erroneous connection edge based on the connection costs, and disconnects the discriminated erroneous connection edge, to thereby generate the plurality of graph structures from the provisional graph structures.

3. An image processing apparatus according to claim 1, wherein the path comprises a shortest path connecting two root nodes that are selected from among the plurality of root nodes to each other.

4. An image processing apparatus according to claim 1, wherein the cost setting unit sets the connection cost for the each of the edges forming the path so that the each of the edges is hard to connect as a distance from the two root nodes becomes larger.

5. An image processing apparatus according to claim 1, wherein the cost setting unit acquires, based on the medical image data, thickness of each of the plurality of linear structures corresponding to the each of the edges forming the path, and sets the connection cost for the each of the edges forming the path so that the each of the edges is hard to connect as the thickness corresponding to the each of the edges becomes smaller.

6. An image processing apparatus according to claim 1, wherein the cost setting unit sets the connection cost for the each of the edges forming the path so that the each of the edges is hard to connect as an angle formed by directional vectors directed from the each of the edges toward the respective two root nodes becomes smaller.

7. An image processing apparatus according to claim 1, wherein the path detection-use graph structure comprises a tree structure having one of the plurality of root nodes as a starting point.

8. An image processing apparatus according to claim 2, wherein the root node extraction unit uses graph matching to compare predetermined shapes representing the plurality of linear structures with the provisional graph structures, to thereby detect the plurality of root nodes from the plurality of nodes.

9. An image processing apparatus according to claim 1, wherein the plurality of linear structures comprise blood vessels of lung or liver.

10. An image processing method for use in an image processing apparatus, comprising a graph structure generation step of generating, based on medical image data including a plurality of linear structures each repeatedly branching from a point of origin and extending in directions away from the point of origin in such a manner as to become wider, graph structures by defining the plurality of linear structures through use of a plurality of nodes and a plurality of edges connecting the plurality of nodes to each other, wherein the graph structure generation step comprises:
 a node extraction step of extracting, based on the medical image data, the plurality of nodes for defining the plurality of linear structures;
 a root node extraction step of extracting, from the extracted plurality of nodes, a plurality of root nodes corresponding respectively to the points of origin of the plurality of linear structures;
 a path detection step of generating a path detection-use graph structure based on the plurality of nodes and detect a path that is included in the generated path detection-use graph structure and connects the plurality of root nodes to each other; and
 a cost setting step of setting, based on a predetermined condition representing a feature of an erroneous connection edge, which erroneously connects two nodes that are to belong to different graph structures to each other, a connection cost for each of edges forming the path so that the erroneous connection edge is hard to connect, and
wherein the graph structure generation step comprises generating, based on the plurality of nodes and the set connection costs, a plurality of graph structures corresponding respectively to the plurality of linear structures.

11. A computer-readable non-transitory recording medium having recorded thereon an image processing program for causing a computer to execute a graph structure generation step of generating, based on medical image data including a plurality of linear structures each repeatedly branching from a point of origin and extending in directions away from the point of origin in such a manner as to become wider, graph structures by defining the plurality of linear structures through use of a plurality of nodes and a plurality of edges connecting the plurality of nodes to each other, wherein the graph structure generation step comprises:

a node extraction step of extracting, based on the medical image data, the plurality of nodes for defining the plurality of linear structures;

a root node extraction step of extracting, from the extracted plurality of nodes, a plurality of root nodes corresponding respectively to the points of origin of the plurality of linear structures;

a path detection step of generating a path detection-use graph structure based on the plurality of nodes and detect a path that is included in the generated path detection-use graph structure and connects the plurality of root nodes to each other; and a cost setting step of setting, based on a predetermined condition representing a feature of an erroneous connection edge, which erroneously connects two nodes that are to belong to different graph structures to each other, a connection cost for each of edges forming the path so that the erroneous connection edge is hard to connect, and wherein the graph structure generation step comprises generating, based on the plurality of nodes and the set connection costs, a plurality of graph structures corresponding respectively to the plurality of linear structures.

\* \* \* \* \*